United States Patent [19]

Anderson et al.

[11] Patent Number: 5,520,302

[45] Date of Patent: May 28, 1996

[54] PETRI DISH HAVING TWO-POSITION LID

[76] Inventors: Roger Anderson, 801 E. Lime, Monrovia, Calif. 91016; Selby T. Hatch, 2321 Hidden Valley Cir., Sandy, Utah 84092

[21] Appl. No.: 189,153

[22] Filed: Jan. 27, 1994

[51] Int. Cl.⁶ .................... B65D 51/16; B65D 21/06; C12M 1/22
[52] U.S. Cl. .............. 220/355; 220/366.1; 206/507; 435/299.1
[58] Field of Search .................... 220/355, 357, 220/358, 366, 282, 228, 366.1; 706/507, 508; 435/297, 298

[56] References Cited

U.S. PATENT DOCUMENTS

| | | | |
|---|---|---|---|
| 3,055,808 | 9/1962 | Henderson | 435/298 |
| 3,234,107 | 2/1966 | Kaufman et al. | |
| 3,632,478 | 1/1972 | Fink . | |
| 3,649,463 | 3/1972 | Buterbaugh . | |
| 3,769,171 | 10/1973 | Grimes et al. | |
| 3,986,935 | 10/1976 | Jackson, Jr. et al. | |
| 4,160,700 | 7/1979 | Boomus et al. | |
| 4,294,924 | 10/1981 | Pepicelli et al. | |
| 4,358,908 | 11/1982 | Song . | |
| 4,668,633 | 5/1987 | Walton | 435/298 |
| 4,670,398 | 6/1987 | Song | 220/366 X |
| 4,675,298 | 6/1987 | Brusewitz . | |
| 4,743,556 | 5/1988 | Ervin . | |
| 5,021,351 | 6/1991 | Ervin . | |
| 5,366,893 | 11/1994 | Stevens et al. | 435/297 X |
| 5,388,714 | 2/1995 | Zutler | 220/366.1 X |

Primary Examiner—Allan N. Shoap
Assistant Examiner—Nathan Newhouse
Attorney, Agent, or Firm—Kelly, Bauersfeld & Lowry

[57] ABSTRACT

A petri dish for the culturing of microorganisms includes a rectangular dish having a floor plate and an endless peripheral dish wall which extends upwardly therefrom, and a two-position lid. The lid includes a ceiling plate, an endless outer peripheral lid wall extending downwardly therefrom, and an endless groove generally adjacent to the outer peripheral lid wall, which corresponds in shape to an upward end of the dish wall. When the lid is oriented in a first position entirely overlying the dish, the upward end of the dish wall is prevented from being fully inserted into the groove so that gas flow is permitted between the lid and the dish. When the lid is turned 180 degrees and placed in a second position entirely overlying the dish, the upward end of the dish wall extends into the groove. This has the effect of severely restricting or preventing gas flow between the lid and the dish. Beads and flanges are integrally molded onto exterior surfaces of the lid and dish to facilitate the stacking of petri dishes one atop another, and handling of the components.

21 Claims, 3 Drawing Sheets

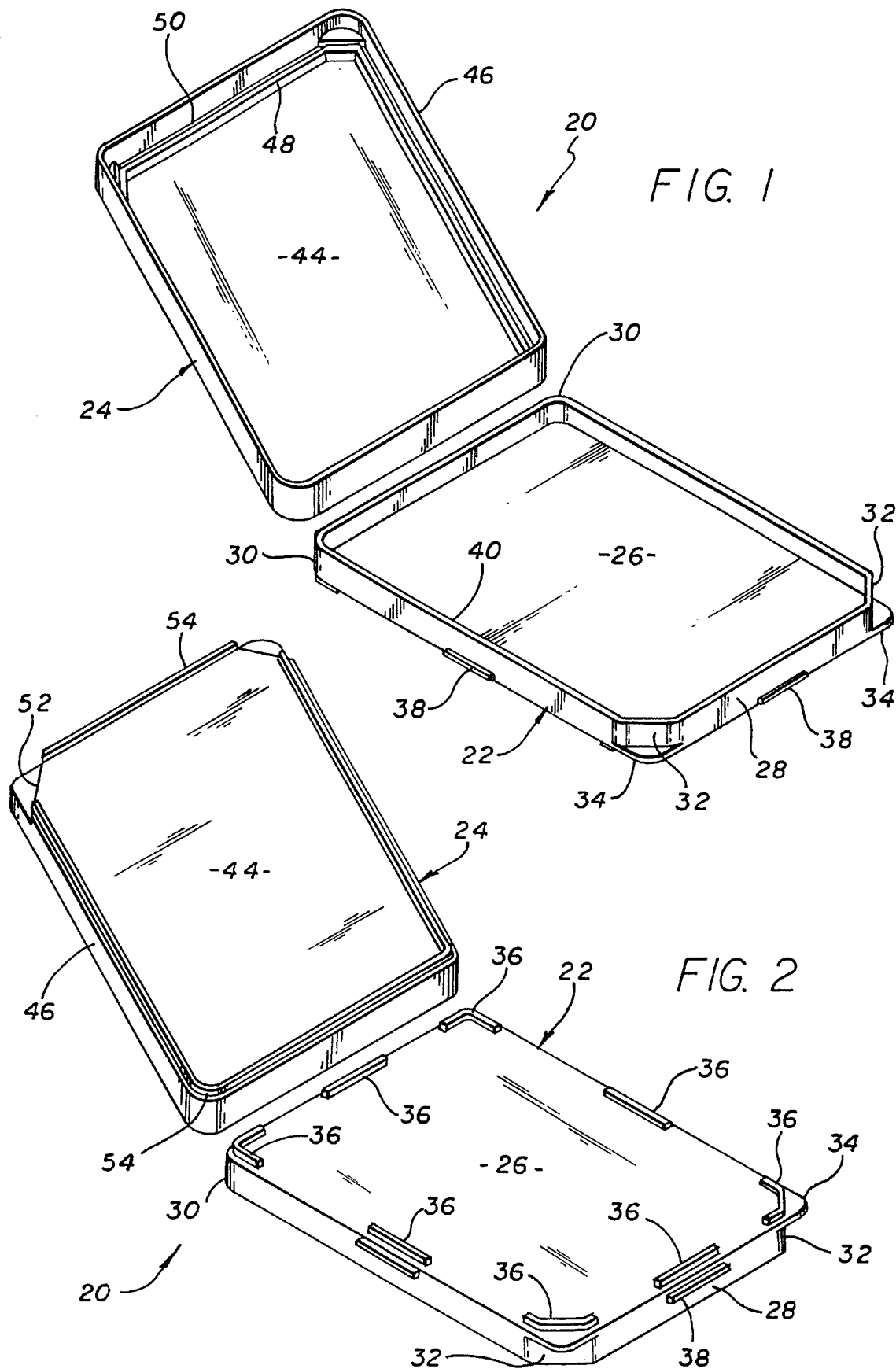

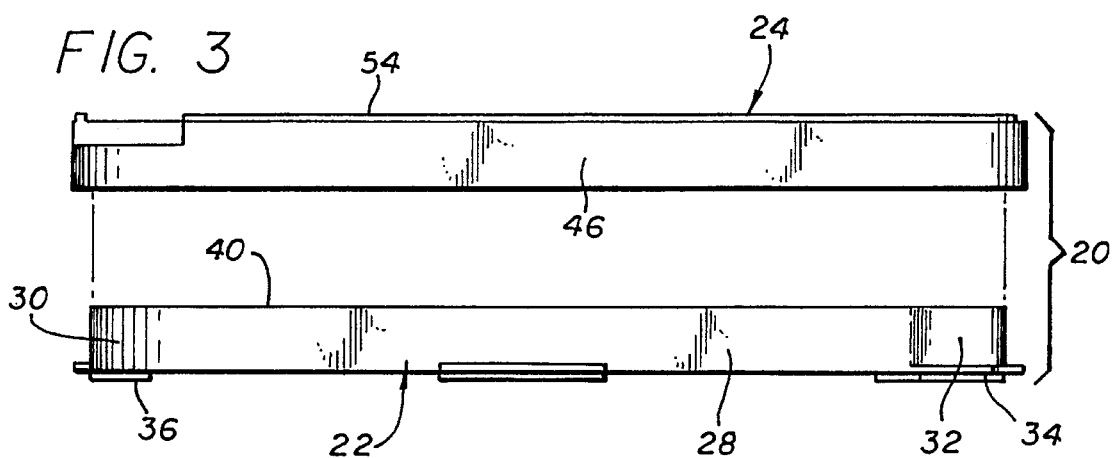
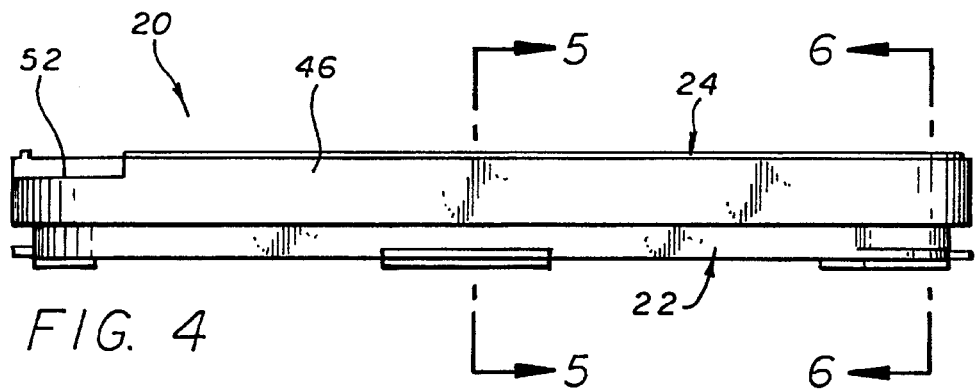
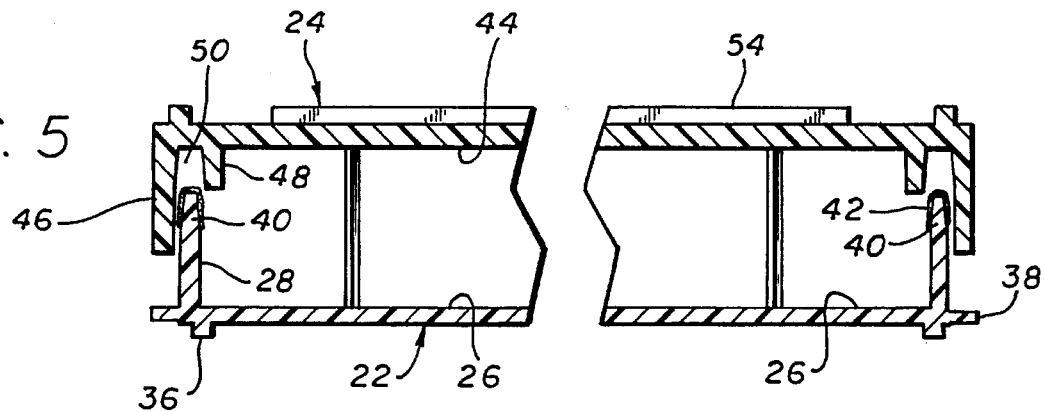
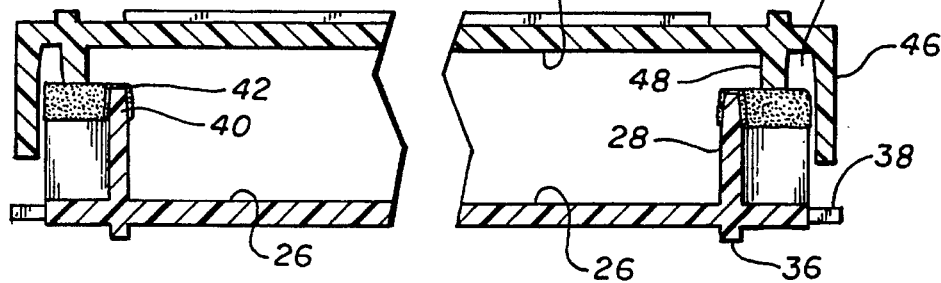

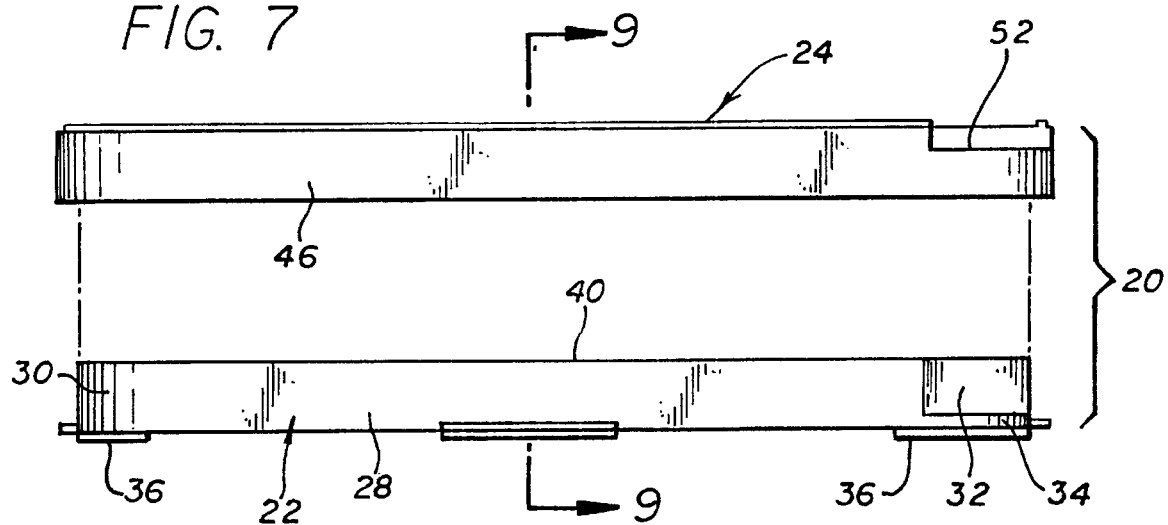
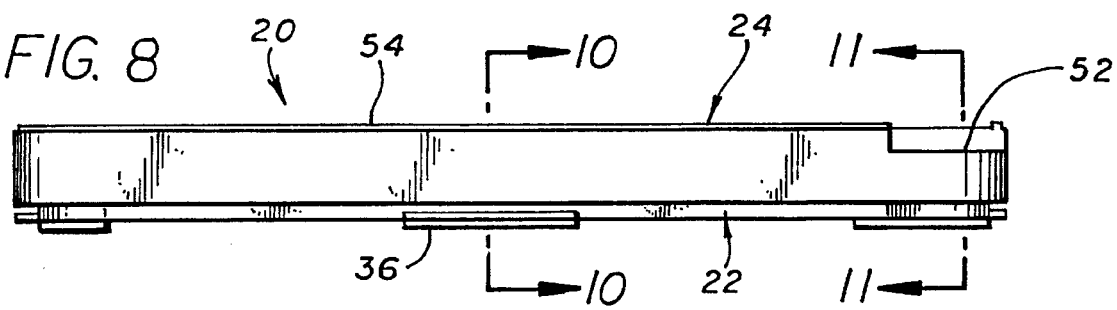
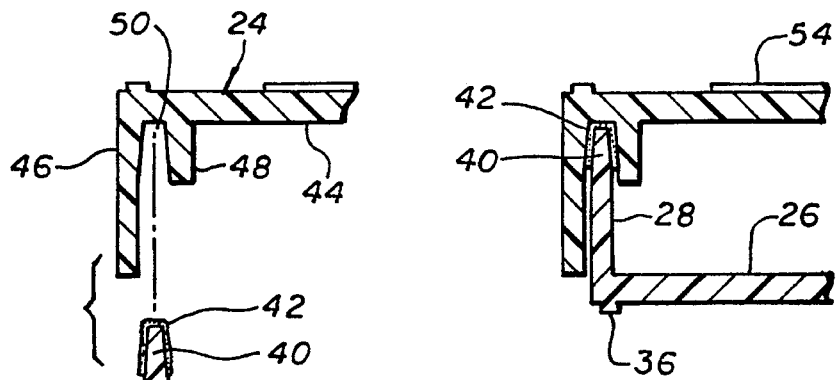
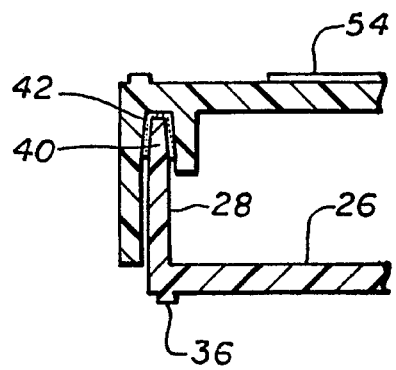
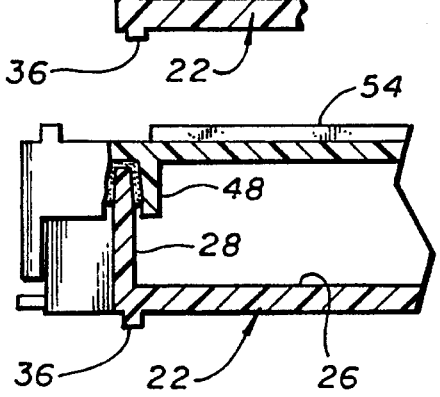

PETRI DISH HAVING TWO-POSITION LID

BACKGROUND OF THE INVENTION

The present invention relates generally to growth containers such as petri dishes. More specifically, the present invention relates to a petri dish having a two-position lid which provides, alternatively, means to permit or prevent gas exchange between the interior of the petri dish and the atmosphere.

The concept of employing what is known as petri dishes for growing bacteria colonies is well known. Petri dishes are often constructed of glass and usually define a circular lower portion which has an upstanding annular wall adapted to contain a material such as agar or gelatin as a culture medium for the bacteria. The lower portion is covered with a similarly shaped cover having a slightly larger diameter so that it encompasses the lower portion. The petri dish has been defined as a small shallow dish of thin glass, with a loosely fitting overlapping cover, used for plate cultures in bacteriology.

Of more recent vintage are the petri dishes constructed of plastic material and, therefore, so inexpensively fabricated that they may be disposed after a single use, thereby eliminating the relatively expensive washing and sterilization process ordinarily required. A plastic type petri dish may be fabricated at the factory and may then have included therein the agar, all under sterile conditions. They can be individually packaged for use in a biological laboratory.

Two types of petri dishes are known, namely, those the covers of which have projections on their inner surfaces and those the covers of which are free of projections on the inner surfaces. Those with projections usually have three small, about 1 to 2 min. high, nub-like projections that lie on the flat edge of the lower dish to prevent the cover from lying closely upon the edge of the lower dish so that a slit is formed through which gas exchange is possible with the inner space of the petri dish. After pouring in a nutrient substrate, especially a gel-like nutrient substrate such as agar, gas exchange is important for the culturing process. In the case of anaerobic culture processes, gas exchange may be important for the removal of oxygen or of the oxygen-containing atmosphere, or for the replacement thereof.

Although the structure of a petri dish is quite simple, it must perform its intended function as efficiently and inexpensively as possible. Ideally, the petri dish should be a shallow rigid container which is easily manipulable by a technician with respect to manual placement and removal of the cover. Also, the petri dish should efficiently receive and distribute liquid nutrient media during the manufacturing process so that a uniform layer of solidified media with a continuous meniscus with the side wall of the bottom container is obtained. In this regard, the interior configuration of the bottom container should not impede the distribution of the liquid nutrient media during filling.

Petri dishes are commonly, but not exclusively, used to culture prokaryotic (i.e., viruses, bacteria and bacteriophage) and eukaryotic (i.e., tissue culture, plant sales, molds, fungi, yeast, microscopic worms and many eggs and embryos) cells or organisms. These cells are grown in a liquid medium or on a solid medium which supplies the needed nutrients to the cells. Other uses include sample storage such as field sample collection, food testing and laboratory experiments.

When dishes are filled with a solid medium they are often stored for days or months before use. Most hospitals and medical clinics buy prefilled dishes which can be as old as six months. Many scientific laboratories have technicians who pour dishes for the entire lab, or the researchers pour their own dishes. In either case, more dishes are poured than are usually needed at the time for convenience. However, the solid medium will dry out if the dishes are not kept in a sealed package or individually wrapped, since the lids are typically designed to allow free gas exchange. After the dishes have been used they can be discarded, but sometimes in laboratory research they are kept and the colonies are used to start new cultures at another time. Again, the petri dishes must be wrapped to prevent dehydration. This can be very tiresome if there are a large number of dishes to be wrapped.

Accordingly, there has been a need for an improved petri dish which can be manufactured inexpensively, maintains all of the principal advantages of prior petri dishes, and yet incorporates features which significantly improve the utility thereof. Such an improved petri dish should preferably permit the technician to grow cultures therein selectively under aerobic or anaerobic conditions, utilizing the same basic components. Further, an improved petri dish is needed which is easily sealed, without wrapping, after filling with a nutrient medium and which, by a mere change in component configuration, may be utilized to grow tissue cultures therein while permitting gas exchange to occur. Moreover, a novel petri dish incorporating the above features should be stable when stacked one atop another and permit parallel or perpendicular stacking arrangements. The present invention fulfills these needs and provides other related advantages.

SUMMARY OF THE INVENTION

The present invention resides in an improved petri dish for the culturing of microorganisms. The petri dish of the present invention comprises, generally, a dish having a floor plate and a peripheral dish wall extending upwardly from the floor plate, and a two-position lid having a ceiling plate and an outer peripheral lid wall which extends downwardly from the ceiling plate. Means are provided for positioning the lid in a first position entirely overlying the dish such that gas flow is permitted between the dish and the lid. Means are also provided for positioning the lid in a second position entirely overlying the dish such that gas flow is severely restricted or altogether prevented between the dish and the lid.

In a preferred form of the invention, the petri dish comprises a rectangular dish having a floor plate and an endless peripheral dish wall extending upwardly from the floor plate. The dish wall has rounded corners at a first end of the dish and notched corners at a second end of the dish. The two-position lid includes a ceiling plate, an endless outer peripheral lid wall extending downwardly from the ceiling plate, an inner peripheral wall extending downwardly from the ceiling plate and spaced inwardly from the outer peripheral lid wall, and an endless groove defined between the outer peripheral lid wall and the inner peripheral lid wall. The groove corresponds in shape to an upward end of the dish wall.

When the lid is placed in a first position entirely overlying the dish, the upward end of the dish wall is prevented from being fully inserted into the groove so that gas flow is permitted between the lid and the dish. In this regard, the notched corners of the dish wall engage a portion of the lid inner peripheral wall to accomplish the intended result when the lid is placed in the first position over the dish. Alternatively, when the dish is placed in a second position entirely overlying the dish, the upward end of the dish wall extends into the groove.

Means are provided for forming a gas-tight seal between the dish and the lid when the lid is placed in the second position over the dish. The seal forming means includes a sealant adhered to the upward end of the dish wall in such a manner so as to prevent gas flow between the lid and the dish when the upward end of the dish wall is fitted within the groove.

Tactile indicia are incorporated into the lid, for positioning the lid in the first or second positions over the dish.

Means are provided for stacking a plurality of petri dishes one atop another. The stacking means includes a peripheral lid bead extending upwardly from the ceiling plate, and a plate bead which extends downwardly from the floor plate. The plate bead and the lid bead are configured so as to prevent relative horizontal sliding movement of the dish when placed atop the lid.

The floor plate is dimensioned to at least correspond to the dimensions of the ceiling plate within the outer peripheral lid wall. Further, tabs extend horizontally outwardly from the peripheral dish wall to facilitate handling of the petri dish.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a petri dish embodying the invention, illustrating the interior configuration of a rectangular dish and a two-position lid;

FIG. 2 is a perspective view of the petri dish shown in FIG. 1, taken from an opposite viewpoint so as to illustrate the external configuration of the dish and the lid;

FIG. 3 is an exploded side elevational view of the petri dish of FIGS. 1 and 2, illustrating the orientation of the lid over the dish prior to being placed thereon in a first position;

FIG. 4 is an elevational view similar to that shown in FIG. 3, illustrating the manner in which the lid is placed over the dish in its first position so as to permit gas flow between the dish and the lid;

FIG. 5 is an enlarged fragmented sectional view taken generally along the line 5—5 of FIG. 4;

FIG. 6 is an enlarged fragmented sectional view taken generally along the line 6—6 of FIG. 4;

FIG. 7 is an exploded side elevational view of the petri dish of FIGS. 1 and 2, illustrating the orientation of the lid prior to being pressed onto the dish in a second position (in comparison with the first position shown in FIGS. 3–6);

FIG. 8 is an elevational view similar to that shown in FIG. 7, illustrating the manner in which the lid, in its second position, is pressed over the dish so as to severely restrict gas flow between the dish and the lid in comparison with gas flow when the lid is placed in the first position (see FIG. 4);

FIG. 9 is an enlarged fragmented sectional view taken generally along the line 9—9 of FIG. 7;

FIG. 10 is an enlarged fragmented sectional view taken generally along the line 10—10 of FIG. 8; and FIG. 11 is an enlarged fragmented sectional view taken generally along the line 11—11 of FIG. 8.

DETAILED DESCRIPTION OF THE PREFERRED EMBODIMENT

As shown in the drawings for purposes of illustration, the present invention is concerned with an improved petri dish, generally designated in the accompanying drawings by the reference number 20. The petri dish 20 comprises, generally, a rectangular dish 22 adapted to rest on a horizontal supporting surface, and an overlying two-position lid 24.

In accordance with the present invention, with reference initially to FIGS. 1 and 2, the rectangular dish 22 includes a planar floor plate 26 and an endless peripheral dish wall 28 which extends upwardly from the floor plate. The dish wall 28 has two rounded corners 30 at one end of the dish 22, and two notched corners 32 at an opposite end of the dish. Tabs 34 which are coplanar with the floor plate 26 extend outwardly from the notched corners 32. Eight plate beads 36 extend downwardly from the floor plate 26 to facilitate the stacking of a plurality of petri dishes 20 one atop another. Further, four handling flanges 38 extend outwardly from the sides of the dish wall 28, to facilitate handling of the petri dish 20.

An upward end 40 of the dish wall 28 includes a sealant 42 adhered thereto. The sealant 42 may be an elastomeric coating applied over the upward end 40 of the dish wall 28 during the manufacturing process.

The two-position lid 24 includes a ceiling plate 44, an endless outer peripheral lid wall 46 which extends downwardly from the ceiling plate, and an inner peripheral wall 48 which also extends downwardly from the ceiling plate 44 and is spaced inwardly from the outer peripheral lid wall 46. An endless groove 50 is defined between the outer peripheral lid wall 46 and the inner peripheral wall 48. The groove 50 corresponds in shape to the upward end 40 of the dish wall 28.

The exterior surface of the lid 24 is configured to provide tactile indicia for positioning the lid into one of two primary positions over the dish 22. For this purpose two lid cut-outs 52 are provided adjacent to the portion of the lid wherein the groove 50 corresponds to the notched corners 32 of the dish wall 28.

The rectangular configuration of the dish 22 and the lid 24 permits the lid to be placed over the dish so as to entirely overlie the dish in only two ways. When the lid 24 is placed in a first position entirely overlying the dish 22 (FIGS. 3–6), the upward end 40 of the dish wall 28 is prevented from being fully inserted into the groove 50 so that gas flow is permitted between the lid and the dish. Alternatively, when the lid 24 is placed in a second position entirely overlying the dish 22 (FIGS. 7–11), the upward end 40 of the dish wall 28 extends into the groove 50. In this configuration, the sealant 42 applied to the upward end 40 of the dish wall 28 seals against the walls of the groove 50 to prevent gas flow between the lid 24 and the dish 22. However, even without the use of the sealant 42, so positioning the upward end 40 of the dish wall 28 within the groove 50 serves to severely restrict gas flow between the dish 22 and the lid 24 in comparison with gas flow when the lid is placed in the first position.

With reference specifically to FIGS. 3–6, the lid 24 is oriented to be placed in its first position over the dish 22 when the lid cut-outs 52 are aligned with the rounded corners 30. When the lid 24 is pressed down upon the dish 22, portions of the upward end 40 of the dish wall 28 are caused to engage a portion of the lid inner peripheral wall 48. This effectively prevents the dish wall 28 from entering the groove 50, thereby ensuring a gap through which gas flow is permitted between the dish 22 and the lid 24.

With reference to FIGS. 7-11, the lid 24 is oriented properly to be pressed over the dish 22 in its second position when the lid cut-outs 52 are aligned with the notched corners 32. Since the dish wall 28 and the groove 50 have the same configuration, the upward end 40 of the dish wall is easily fitted into the groove to severely restrict gas flow, or altogether prevent it, between the dish and the lid. Advantageously, a nutrient base placed within the dish 22 is far less likely to dry out and become unusable when the dish 22 and the lid 24 are so sealed together. Such a seal also eliminates the need for wrapping the petri dish 20.

A peripheral lid bead 54 extends upwardly from the ceiling plate 44 and is located such that when a plurality of petri dishes are stacked one atop another, the plate beads 36 and the lid bead 54 cooperatively prevent relative horizontal sliding movement of the dish 22 when placed atop the lid 24. Notably, the arrangement of the lid beads 54 and the plate beads 36 permit the petri dishes 20 to be either stacked in alignment with one another, or perpendicularly with respect to one another. In either case, stability is facilitated by placement of the lid beads 54 and the plate beads 36.

In some instances it is desirable to stack several dishes 22 one atop another, and utilize only one lid 24 over the uppermost dish 22. In such cases it is still desirable to cover the interior of the dish 22 to prevent contamination thereof. For this reason, as well as to facilitate handling of the dish 22, the tabs 34 are provided. In a sense, the tabs 34 are an extension of the floor plate 26 which preferably is dimensioned to at least correspond to the dimensions of the ceiling plate 44 within the outer peripheral lid wall 46.

From the foregoing, it is to be appreciated that the improved petri dish 20 of the present invention has far greater utility than standard petri dishes in that the two-position lid 24 can be fitted over the dish 22 to either permit gas flow between the dish and the lid, or to prevent gas flow therebetween altogether. The petri dish 20 disclosed herein may be manufactured simply and inexpensively, utilizing standard materials. Moreover, the rectangular configuration of the petri dish 20 shown in the accompanying drawings lends itself well to modern culture photography techniques, as well as to handling by robotic automated systems.

Although a particular embodiment of the invention has been described in detail for purposes of illustration, various modifications may be made without departing from the spirit and scope of the invention. Accordingly, the invention is not to be limited, except as by the appended claims.

We claim:

1. A petri dish for the culturing of microorganisms, comprising:

a rectangular dish having a floor plate and a peripheral dish wall extending upwardly from the floor plate; and a two-position lid having a ceiling plate, an outer peripheral lid wall extending downwardly from the ceiling plate, an inner peripheral wall extending downwardly from the ceiling plate and spaced inwardly from the outer peripheral lid wall to define a groove therebetween corresponding in shape to an upward end of the peripheral dish wall, means for positioning the lid in a first position entirely overlying the dish such that gas flow is permitted between the dish and the lid, and means for positioning the lid in a second position entirely overlying the dish such that gas flow is severely restricted between the dish and the lid in comparison with gas flow when the lid is placed in the first position, wherein the upward end of the dish wall slides into the groove when the lid is placed over the dish in the second position, and the upward end of the dish wall is prevented from completely engaging the groove when the lid is placed over the dish in the first position, and wherein the peripheral dish wall includes at least one notched corner configured to engage a portion of the lid inner peripheral wall when the lid is placed over the dish in the first position.

2. The petri dish of claim 1, including means for forming a gas-tight seal between the dish and the lid when the lid is placed in the second position over the dish.

3. The petri dish of claim 2, wherein the seal forming means includes a sealant adhered to the upward end of the dish wall in such a manner so as to prevent gas flow between the lid and the dish when the upward end of the dish wall is fitted within the groove.

4. The petri dish of claim 1, wherein the floor plate is dimensioned to at least correspond to the dimensions of the ceiling plate within the outer peripheral lid wall.

5. The petri dish of claim 1, wherein the lid includes tactile indicia for positioning the lid in the first or second positions over the dish.

6. The petri dish of claim 1, including means for stacking a plurality of petri dishes one atop another.

7. The petri dish of claim 6, wherein the stacking means includes a peripheral lid bead extending upwardly from the ceiling plate, and a plate bead extending downwardly from the floor plate, wherein the plate bead and the lid bead are placed so as to prevent relative horizontal sliding movement of the dish when placed atop the lid.

8. The petri dish of claim 7, including handling tabs extending horizontally outwardly from the peripheral dish wall.

9. A petri dish, comprising:

a dish having a floor plate and an endless peripheral dish wall extending upwardly from the floor plate, the dish wall having a different configuration at a first end of the dish in comparison with a configuration of the dish wall at a second end of the dish; and a lid pressed onto the dish in one of two possible positions, having a ceiling plate, an endless outer peripheral lid wall extending downwardly from the ceiling plate, and an inner peripheral wall extending downwardly from the ceiling plate and spaced inwardly from the outer peripheral lid wall to define therebetween an endless groove which corresponds in shape to an upward end of the dish wall;

wherein when the lid is placed in a first position entirely overlying the dish, the upward end of the dish wall is prevented from being fully inserted into the groove, and when the dish is placed in a second position entirely overlying the dish, the upward end of the dish wall extends into the groove; and wherein the peripheral dish wall includes at least one notched corner configured to engage a portion of the lid inner peripheral wall when the lid is placed over the dish in the first position.

10. The petri dish of claim 9, including means for forming a gas-tight seal between the dish and the lid when the lid is placed in the second position over the dish, the seal forming means including a sealant adhered to the upward end of the dish wall in such a manner so as to prevent gas flow between the lid and the dish when the upward end of the dish wall is fitted within the groove.

11. The petri dish of claim 9, wherein the dish has a generally rectangular configuration, gas flow is permitted between the lid and the dish when the lid is placed in the first position over the dish, and wherein gas flow is severely restricted between the dish and the lid when the lid is placed in the second position over the dish, in comparison with gas flow when the lid is placed in the first position.

12. The petri dish of claim 9, wherein the lid includes tactile indicia for positioning the lid in the first or second positions over the dish.

13. The petri dish of claim 9, including means for stacking a plurality of petri dishes one atop another, the stacking means including a peripheral lid bead extending upwardly from the ceiling plate, and a plate bead extending downwardly from the floor plate, wherein the plate bead and the lid bead are placed so as to prevent relative horizontal sliding movement of the dish when placed atop the lid.

14. A petri dish for the culturing of microorganisms, comprising:

a rectangular dish having a floor plate and an endless peripheral dish wall extending upwardly from the floor plate, the dish wall having rounded corners at a first end of the dish and notched corners at a second end of the dish;

a two-position lid having a ceiling plate, an endless outer peripheral lid wall extending downwardly from the ceiling plate, an inner peripheral wall extending downwardly from the ceiling plate and spaced inwardly from the outer peripheral lid wall, and an endless groove defined between the outer peripheral lid wall and the inner peripheral wall, the groove corresponding in shape to an upward end of the dish wall, wherein when the lid is placed in a first position entirely overlying the dish, the upward end of the dish wall is prevented from being fully inserted into the groove such that gas flow is permitted between the lid and the dish, and wherein when the lid is placed in a second position entirely overlying the dish, the upward end of the dish wall extends into the groove;

means for forming a gas-tight seal between the dish and the lid when the lid is placed in the second position over the dish;

tactile indicia incorporated into the lid, for positioning the lid in the first or second positions over the dish; and means for stacking a plurality of petri dishes one atop another.

15. A petri dish for the culturing of microorganisms, comprising:

a rectangular dish having a floor plate and a peripheral dish wall extending upwardly from the floor plate; and a two-position lid having a ceiling plate, an outer peripheral lid wall extending downwardly from the ceiling plate, means for positioning the lid in a first position entirely overlying the dish such that gas flow is permitted between the dish and the lid, means for positioning the lid in a second position entirely overlying the dish and turned 180 degrees relative to the first position such that gas flow is severely restricted between the dish and the lid in comparison with gas flow when the lid is placed in the first position, and a groove generally adjacent to the outer peripheral lid wall and corresponding in shape to an upward end of the peripheral dish wall, wherein the upward end of the dish wall slides into the groove when the lid is placed over the dish in the second position, and wherein the upward end of the dish wall is prevented from completely engaging the groove when the lid is placed over the dish in the first position.

16. The petri dish of claim 15, including means for forming a gas-tight seal between the dish and the lid when the lid is placed in the second position over the dish, wherein the seal forming means includes a sealant adhered to the upward end of the dish wall in such a manner so as to prevent gas flow between the lid and the dish when the upward end of the dish wall is fitted within the groove.

17. The petri dish of claim 15, wherein the peripheral dish wall includes at least one notched corner configured to engage a portion of the lid when the lid is placed over the dish in the first position to prevent the upward end of the dish wall from completely engaging the groove.

18. The petri dish of claim 15, including means for stacking a plurality of petri dishes one atop another, wherein each successively stacked dish functions as a lid for the lower adjacent dish such that a two-position lid is required only to cover a top one of the stacked dishes.

19. A petri dish, comprising:

a rectangular dish having a floor plate and an endless peripheral dish wall extending upwardly from the floor plate; and a two-position lid having a ceiling plate and an endless groove corresponding in shape to an upward end of the dish wall, wherein when the lid is placed in a first position entirely overlying the dish, an upward end of the dish wall is prevented from being fully inserted into the groove such that gas flow is permitted between the lid and the dish, and wherein when the lid is placed in a second position entirely overlying the dish and turned 180 degrees relative to the first position, the upward end of the dish wall extends into the groove.

20. The petri dish of claim 19, wherein the two-position lid includes an endless outer peripheral lid wall extending downwardly from the ceiling plate, and an inner peripheral wall extending downwardly from the ceiling plate and spaced inwardly from the outer peripheral lid wall to define the endless groove.

21. The petri dish of claim 20, wherein the dish wall includes at least one notched corner which, when the two-positioned lid is placed in its second position, extends into the groove, and which, when the lid is placed in its first position, engages a portion of the lid so as to be unable to be fully inserted into the groove.

* * * * *